United States Patent
McLean et al.

(10) Patent No.: US 6,940,659 B2
(45) Date of Patent: Sep. 6, 2005

(54) CONE-SHAPED LENS HAVING INCREASED FORWARD LIGHT INTENSITY AND KITS INCORPORATING SUCH LENSES

(75) Inventors: Bruce S. McLean, Sandy, UT (US); Vasiliy Nosov, Moscow (RU); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/328,510

(22) Filed: Dec. 23, 2002

(65) Prior Publication Data

US 2003/0142413 A1 Jul. 31, 2003

Related U.S. Application Data

(63) Continuation-in-part of application No. 10/044,346, filed on Jan. 11, 2002.

(51) Int. Cl.[7] .......................... G02B 3/02; G02B 13/18; A61C 1/00; A61C 3/00
(52) U.S. Cl. ......................................... 359/709; 433/29
(58) Field of Search ................................ 359/707–712, 359/809; 433/29–31

(56) References Cited

U.S. PATENT DOCUMENTS

| | | |
|---|---|---|
| 3,310,358 A | 3/1967 | Marcatili .................... 350/189 |
| 3,704,928 A | 12/1972 | Coombs et al. |
| 3,930,149 A | 12/1975 | French |
| 4,184,196 A | 1/1980 | Moret et al. .................. 433/29 |
| 4,221,994 A | 9/1980 | Friedman et al. ........... 315/224 |
| 4,229,658 A | 10/1980 | Gonser |
| 4,245,890 A | 1/1981 | Hartman et al. ............ 350/175 |
| 4,266,535 A | 5/1981 | Moret |
| 4,281,366 A | 7/1981 | Wurster et al. ............... 362/32 |
| 4,309,617 A | 1/1982 | Long |

(Continued)

FOREIGN PATENT DOCUMENTS

WO  WO 99/35995  7/1999

OTHER PUBLICATIONS

U.S. Appl. No. 10/073,822, filed Feb. 11, 2002.
U.S. Appl. No. 10/073,823, filed Feb. 11, 2002.
"Dental/Medical Diagnostic Systems, Inc. Received $4.0 Million Order for Its Wireless Apollo e and Wavelight Curing Units Based on New LED Technology", www.compoundsemiconductor.net (Nov. 20, 2000).
"Just Cure It", Air Tecniques, Inc. (Jan. 25, 2002).
"LUXoMAX the Latest News from Akeda Dental", Akeda Dental A/S, www.akeda.dk (Oct. 1, 2001).
"NRG L.E.D. Curing Light", Dentsply Caulk (Oct. 2001).
"Optilux 180 & 360 Polymerization Units (Projects 98–17 & 98–18)", Kerr/Demetron (Jan. 23, 2002).
"Resin Curing Lights: What You Should Know", Contemporary Esthetics and Restorative Practice, p. 36 (Nov. 2001).
"Specturm 800 Curing Unit (Project 99–13)" L.D. Caulk Division, Dentsply International, Inc. (Jan. 23, 2002).
"The Power PAC", American Dental Technologies, www.americandentaltech.com (Jan. 23, 2002).
"ZAP Dual Curing Light (Project 01–26)", CSM–Dental (Denmark)/Soft–core Texas, Inc. (Jan. 23, 2002).

* cited by examiner

Primary Examiner—Georgia Epps
Assistant Examiner—Alicia M. Harrington
(74) Attorney, Agent, or Firm—Workman Nydegger

(57) ABSTRACT

The invention is directed to lenses having thin walls and a generally conical shape for use with dental light-curing devices. The conical or otherwise tapered shape enables the apex of the lenses to be inserted at least partially within a dental preparation (e.g., a Class II dental preparation). The thin walls allow the light emitted from the light-curing device to pass through the lens and apex without being undesirably refracted, thereby enabling light to be emitted directly in front of the apex with sufficient intensity to cure light-curable compounds within the dental preparation.

28 Claims, 2 Drawing Sheets

U.S. PATENT DOCUMENTS

| | | |
|---|---|---|
| 4,348,180 A | 9/1982 | Schuss |
| 4,392,827 A | 7/1983 | Martin |
| 4,522,594 A | 6/1985 | Stark et al. |
| 4,611,992 A | 9/1986 | Lokken |
| 4,666,405 A | 5/1987 | Ericson ............... 433/229 |
| 4,666,406 A | 5/1987 | Kanca, III ............ 433/229 |
| 4,682,950 A | 7/1987 | Dragan |
| 4,698,730 A | 10/1987 | Sakai et al. ............ 362/311 |
| 4,733,937 A | 3/1988 | Lia et al. ............ 350/96.26 |
| 4,836,782 A | 6/1989 | Gonser |
| 4,935,665 A | 6/1990 | Murata ............... 313/500 |
| 4,948,215 A | 8/1990 | Friedman |
| 4,963,798 A | 10/1990 | McDermott ............ 315/312 |
| 4,992,045 A | 2/1991 | Beisel |
| 5,013,144 A | 5/1991 | Silverglate et al. ...... 350/435 |
| 5,013,240 A | 5/1991 | Bailey et al. |
| 5,017,140 A | 5/1991 | Ascher |
| 5,043,634 A | 8/1991 | Rothwell, Jr. et al. |
| 5,071,222 A | 12/1991 | Laakmann et al. ...... 385/125 |
| 5,115,761 A | 5/1992 | Hood |
| 5,123,845 A | 6/1992 | Vassiliadis et al. ...... 433/215 |
| 5,139,495 A | 8/1992 | Daikuzono ............ 606/17 |
| 5,161,879 A | 11/1992 | McDermott ............ 362/206 |
| 5,275,564 A | 1/1994 | Vassiliadis et al. ...... 433/226 |
| 5,285,318 A * | 2/1994 | Gleckman ............ 359/709 |
| 5,288,231 A | 2/1994 | Kuehn et al. |
| 5,290,169 A | 3/1994 | Friedman et al. |
| 5,312,249 A | 5/1994 | Kennedy |
| 5,328,368 A | 7/1994 | Lansing et al. .......... 433/116 |
| 5,348,552 A | 9/1994 | Nakajima et al. ........ 606/13 |
| 5,371,826 A | 12/1994 | Friedman |
| 5,382,799 A | 1/1995 | May |
| 5,388,988 A * | 2/1995 | Goisser et al. .......... 433/29 |
| 5,397,892 A | 3/1995 | Abdelqader |
| 5,415,543 A | 5/1995 | Rozmajzl, Jr. |
| 5,420,768 A | 5/1995 | Kennedy ............... 362/119 |
| D361,382 S | 8/1995 | Brunsell et al. |
| 5,448,323 A | 9/1995 | Clark et al. |
| 5,457,611 A | 10/1995 | Verderber ............ 362/572 |
| 5,485,317 A | 1/1996 | Perissinotto et al. ...... 359/712 |
| 5,521,392 A | 5/1996 | Kennedy et al. |
| 5,527,261 A | 6/1996 | Monroe et al. |
| 5,616,141 A | 4/1997 | Cipolla ............... 606/15 |
| 5,634,711 A | 6/1997 | Kennedy et al. ........ 362/119 |
| 5,660,461 A | 8/1997 | Ignatius et al. |
| 5,669,769 A | 9/1997 | Disel |
| D385,051 S | 10/1997 | Wu ............... D26/2 |
| D385,360 S | 10/1997 | Benaron |
| 5,698,866 A | 12/1997 | Doiron et al. .......... 257/99 |
| 5,711,665 A | 1/1998 | Adam et al. ............ 433/9 |
| 5,733,029 A | 3/1998 | Monroe |
| 5,749,724 A | 5/1998 | Cheng |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott ............ 362/245 |
| 5,791,898 A | 8/1998 | Maissami ............ 433/164 |
| 5,797,740 A | 8/1998 | Lundvik ............... 433/29 |
| 5,803,729 A | 9/1998 | Tsimerman |
| 5,880,839 A | 3/1999 | Ishizuka et al. |
| 5,885,082 A | 3/1999 | Levy |
| 5,905,268 A | 5/1999 | Garcia et al. |
| 5,908,294 A | 6/1999 | Schick et al. |
| 5,908,295 A | 6/1999 | Kawata ............... 433/29 |
| 5,912,470 A | 6/1999 | Eibofner et al. |
| 5,921,777 A | 7/1999 | Dorman |
| 5,971,755 A * | 10/1999 | Liebermann et al. ...... 433/29 |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,599 A * | 2/2000 | Volcker et al. ............ 433/29 |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,089,740 A | 7/2000 | Forehand et al. |
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. |
| 6,155,823 A | 12/2000 | Nagel |
| 6,159,005 A | 12/2000 | Herold et al. |
| 6,200,134 B1 | 3/2001 | Kovac et al. |
| 6,208,788 B1 | 3/2001 | Nosov |
| 6,270,343 B1 | 8/2001 | Martin |
| 6,280,187 B1 | 8/2001 | Slone ............... 433/29 |
| 6,282,013 B1 | 8/2001 | Ostler et al. |
| 6,318,996 B1 | 11/2001 | Melikechi et al. ......... 433/29 |
| 6,322,358 B1 | 11/2001 | Senn et al. |
| 6,325,623 B1 | 12/2001 | Melnyk et al. ........... 433/29 |
| 6,328,456 B1 | 12/2001 | Mize ............... 362/311 |
| 6,331,111 B1 | 12/2001 | Cao ............... 433/29 |
| 6,361,192 B1 | 3/2002 | Fussell et al. |
| 6,361,489 B1 | 3/2002 | Tsai |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 | 7/2002 | Adam et al. |
| 6,439,888 B1 | 8/2002 | Boutoussov et al. |
| 6,465,961 B1 | 10/2002 | Cao |
| 6,468,077 B1 | 10/2002 | Melikechi et al. |
| 6,478,447 B2 | 11/2002 | Yen |
| 6,482,004 B1 | 11/2002 | Senn et al. |
| 6,485,301 B1 | 11/2002 | Gemunder et al. |
| 6,511,317 B2 | 1/2003 | Melikechi et al. ......... 433/29 |
| 6,511,321 B1 | 1/2003 | Trushkowsky et al. |
| 6,514,075 B1 | 2/2003 | Jacob |
| 6,611,110 B1 | 8/2003 | Fregoso |
| 6,692,251 B1 | 2/2004 | Logan et al. |
| 6,692,252 B2 | 2/2004 | Scott |
| 6,709,128 B2 | 3/2004 | Gordon et al. |
| 6,719,558 B2 | 4/2004 | Cao |
| 6,719,559 B2 | 4/2004 | Cao |
| 6,755,648 B2 | 6/2004 | Cao |
| 6,755,649 B2 | 6/2004 | Cao |
| 2001/0038992 A1 | 11/2001 | Otsuka |
| 2001/0046652 A1 | 11/2001 | Ostler et al. |
| 2001/0055451 A1 | 12/2001 | Kuhara et al. |
| 2002/0073921 A1 | 6/2002 | Russell et al. |
| 2002/0085372 A1 | 7/2002 | Lehrer |
| 2002/0093833 A1 | 7/2002 | West |
| 2002/0115037 A1 | 8/2002 | Cao ............... 433/29 |
| 2002/0133970 A1 | 9/2002 | Gordon et al. ............ 34/250 |
| 2002/0147383 A1 | 10/2002 | Weber et al. |
| 2002/0163317 A1 | 11/2002 | Cao ............... 315/291 |
| 2002/0167283 A1 | 11/2002 | Cao ............... 315/291 |
| 2002/0168603 A1 | 11/2002 | Cao ............... 433/29 |
| 2002/0168604 A1 | 11/2002 | Cao ............... 433/29 |
| 2002/0168605 A1 | 11/2002 | Cao ............... 433/29 |
| 2002/0168606 A1 | 11/2002 | Cao ............... 433/29 |
| 2002/0168607 A1 | 11/2002 | Cao ............... 433/29 |
| 2002/0168608 A1 | 11/2002 | Cao |
| 2002/0172912 A1 | 11/2002 | Cao ............... 433/29 |

| | | | | | | |
|---|---|---|---|---|---|---|
| 2002/0172913 A1 | 11/2002 | Cao | 433/29 | 2003/0036031 A1 | 2/2003 | Lieb et al. | |
| 2002/0172914 A1 | 11/2002 | Cao | 433/29 | 2003/0038291 A1 | 2/2003 | Cao | |
| 2002/0172915 A1 | 11/2002 | Cao | 433/29 | 2003/0039119 A1 | 2/2003 | Cao | 362/227 |
| 2002/0172916 A1 | 11/2002 | Cao | 433/29 | 2003/0039120 A1 | 2/2003 | Cao | 362/227 |
| 2002/0172917 A1 | 11/2002 | Cao | 433/29 | 2003/0039122 A1 | 2/2003 | Cao | 362/294 |
| 2002/0175352 A1 | 11/2002 | Cao | 257/258 | 2003/0040200 A1 | 2/2003 | Cao | 438/800 |
| 2002/0175628 A1 | 11/2002 | Cao | 315/56 | 2003/0081430 A1 | 5/2003 | Becker | |
| 2002/0177095 A1 | 11/2002 | Cao | 433/29 | 2003/0133203 A1 | 7/2003 | McLean et al. | |
| 2002/0177096 A1 | 11/2002 | Cao | | 2003/0133298 A1 | 7/2003 | Cao | |
| 2002/0177099 A1 | 11/2002 | Cao | 433/29 | 2003/0142413 A1 | 7/2003 | McLean et al. | |
| 2002/0180368 A1 | 12/2002 | Cao | 315/149 | 2003/0147254 A1 | 8/2003 | Yoneda et al. | |
| 2002/0181947 A1 | 12/2002 | Cao | 392/409 | 2003/0147258 A1 | 8/2003 | Fischer et al. | |
| 2002/0182561 A1 | 12/2002 | Cao | 433/29 | 2003/0148242 A1 | 8/2003 | Fischer et al. | |
| 2002/0182562 A1 | 12/2002 | Cao | 433/29 | 2003/0152885 A1 | 8/2003 | Dinh | |
| 2002/0187454 A1 | 12/2002 | Mclikechi et al. | | 2003/0186195 A1 | 10/2003 | Comfort et al. | |
| 2002/0187455 A1 | 12/2002 | Melikechi et al. | | 2003/0218880 A1 | 11/2003 | Brukilacchio | |
| 2002/0190659 A1 | 12/2002 | Cao | 315/149 | 2003/0219693 A1 | 11/2003 | Cao | |
| 2002/0190660 A1 | 12/2002 | Cao | 315/149 | 2003/0219694 A1 | 11/2003 | Bianchetti et al. | |
| 2002/0197582 A1 | 12/2002 | Cao | 433/29 | 2003/0235800 A1 | 12/2003 | Qadar | |
| 2003/0001507 A1 | 1/2003 | Cao | 315/56 | 2004/0033033 A1 | 2/2004 | Hoshino et al. | |

CONE-SHAPED LENS HAVING INCREASED FORWARD LIGHT INTENSITY AND KITS INCORPORATING SUCH LENSES

CROSS-REFERENCE TO RELATED APPLICATIONS

The present application is a continuation-in-part of U.S. patent application Ser. No. 10/044,346, filed Jan. 11, 2002 entitled "Optical Lens Used to Focus Light," which is incorporated herein by reference in its entirety.

BACKGROUND OF THE INVENTION

1. The Field of the Invention

The present invention is in the field of light curing devices and, more particularly, to the field of lenses configured for use with dental light-curing devices.

2. The Relevant Technology

In the dental industry, dental cavities are often filled and sealed with photosensitive compounds that are cured by exposure to radiant energy, such as visible light. These compounds, commonly referred to as light-curable compounds, are placed within dental cavity preparations and onto dental surfaces where they are subsequently irradiated by light.

The radiated light causes photosensitive components within the compounds to polymerize, thereby hardening the light-curable compounds within the dental cavity preparation or another desired location.

The light is typically directed to the light-curable compounds with a light-curing device that includes a lamp, such as a halogen lamp bulb, or a Light-Emitting Diode (LED) that is configured to generate light within a spectrum suitable for curing the light-curable dental compounds. Light curing devices also typically include a light guide, such as a fiber optic wand, or a specialized tip or lens that can capture, collimate or otherwise redirect the light within the patient's mouth, where the light is finally dispersed.

One problem with existing light curing devices, however, is that the light-guides are often unable to properly direct the dispersed light to the desired location within the patient's mouth and in the desired manner. For instance, some light guides are unable to properly direct the light within a contained area where the light-curable compounds are located. This is a particularly true of many LED light-curing devices because of the wide angle of dispersion in which LEDs emit light. This is a problem because the improperly dispersed light may irritate sensitive mouth tissues and prevent the light-curable compounds from curing properly.

During certain dental procedures, such as treatment of deep Class II fillings, it is necessary for the light to be directed deep into the dental preparation and with sufficient intensity to cure the light-curable compounds placed therein. To facilitate the dispersion of light within a Class II preparation, or any other deep preparation, it is sometimes desirable to use a cone-shaped tip or lens that can be inserted within the dental preparation, thereby enabling the radiated light to be dispersed within the desired treatment area.

FIG. 1 illustrates one example of an existing conical lens 10 that may be utilized with a light-curing device to help disperse light within a dental preparation. One problem experienced with this existing lens 10, however, is that it can cause the light to be dispersed from the lens 10 in such a manner that a pocket or void 12 of light occurs directly in front of the lens 10, as shown. This void 12 is undesirable because it can effectively prevent curing of any light-curable compound disposed directly in front of the lens 10 during the irradiation procedure, thereby preventing uniform curing of the light-curable compounds within the dental preparation. The void 12 of light that occurs directly in front of the lens 10 is an observable result of Snell's law in which light is refracted by the materials through which the light travels. Snell's law is well-known to those of ordinary skill in the art. The angle at which the light is refracted by the lens is a function of both the material properties (e.g., index of refraction) of the lens 10 and the angle at which the light intersects the outer surface of the lens 10 (e.g., angle of incidence).

In view of the foregoing, there is currently a need in the art for improved tips that can be used with light-curing devices for curing light-curable compounds during dental procedures, particularly for use in Class II dental procedures.

SUMMARY OF PRESENTLY PREFERRED EMBODIMENTS

Briefly summarized, the present invention is directed to an improved lens for LED light-curing devices that enables light to be emitted through the lens with desired forward intensity.

According to one embodiment, the lens of the invention comprises a hollow body that has a substantially conical profile and that defines a substantially conical void that exists within the hollow body. The hollow body of the lens also includes a base that circumferentially extends around the body. In one embodiment, the base is configured to be connected with a light-curing device in such a manner that light emitted from the light-curing device is able to pass through the lens during normal use. The type of connection between the lens and the light-curing device may include a snap-fit, a friction fit, a threaded fitting, and other similar couplings.

The body of the lens includes a thin wall that extends out of the base and converges at an apex, such that the profile of the body is substantially conical. The wall and the apex have a substantially uniform thickness, such that light emitted from the light-curing device in a forward direction is able to pass through the wall and apex without being undesirably refracted by the lens. In one embodiment, the thickness of the lens in the wall and apex regions is a thickness within the range of between about 1.0 mm and about 3.0 mm.

The lens is preferably composed of a transparent material selected from the group including aluminum dioxide, sapphire, quartz, glass and plastic. Any transparent plastic may be used including, but not limited to, acrylic, polyacrylic, polypropylene, polycarbonate, and silicone. Although transparent, the lens may be tinted to filter undesired light emissions.

In summary, the lens of the invention comprises a body that is configured to be inserted at least partially within a dental preparation, such as a Class II preparation, while enabling light to be emitted directly in front of the lens without being undesirably refracted by the lens.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the light-curing device of the invention will now be provided with specific reference to figures illustrating preferred embodiments of the invention. It will be appreciated that like structures will be provided with like reference designations. To provide context for interpreting the scope of the invention, certain terms used throughout the application will now be defined.

The term "Class II," as used herein, is made in reference to Class II Mesio-Occlusal caries and preparations that extend deep into the dental tissue. However, the invention is not limited to lenses that may be used only when treating Class II caries. Class II preparations are typically at least 5 mm deep. However, the invention extends more broadly to any lens, as described herein, that is configured to be inserted at least partially within any dental preparation, regardless of the depth of the dental preparation.

The terms "lens" and "protective lens", as defined herein, refer to any object through which light may travel and does not inherently imply any characteristics for focusing or collimating light. The term lens is sometimes used interchangeably herein with the terms "tip" and "light guide."

Figure 2:
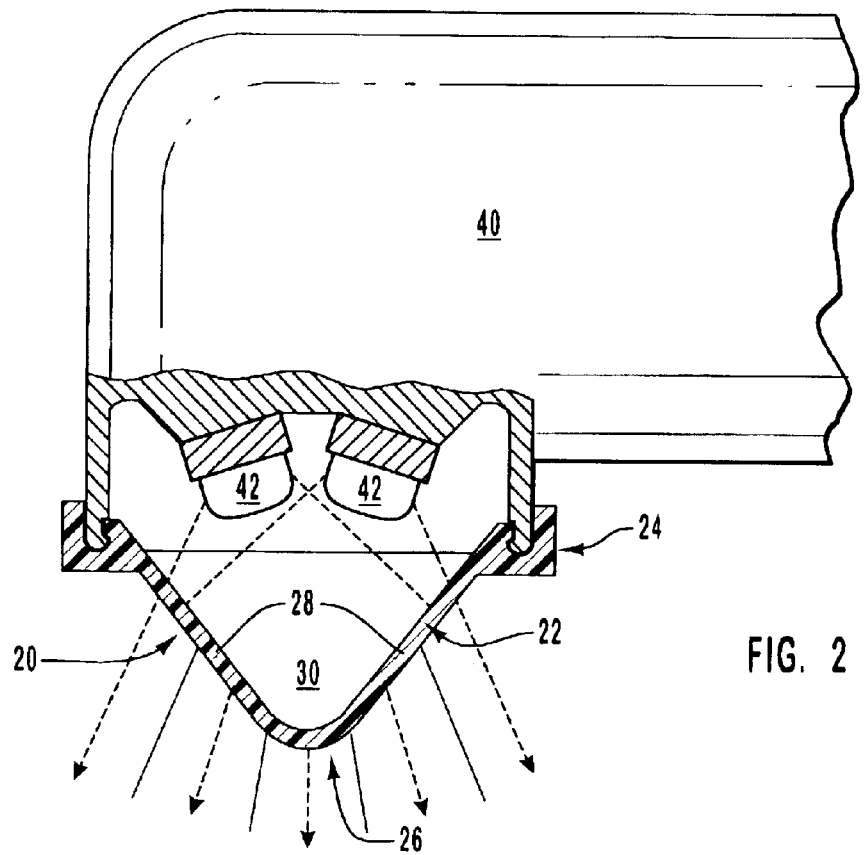
FIG. 2 illustrates one embodiment of a lens according to the invention that includes a hollow body and thin walls that converge at an apex from a base that circumferentially extends around the body of the lens.

FIG. 2 illustrates one embodiment of a protective lens 20 of the invention. As shown, the lens 20 includes a hollow body 22 having a substantially conical profile to enable the lens 20 to be inserted at least partially within a dental preparation, as mentioned above. The hollow body 22 extends from a base 24, which circumferentially extends around the body 22, to an apex 26. A thin wall 28 extends out from the base 24 and converges at an apex 26, defining a conical void 30 therebetween.

In one embodiment, the wall 28 and the apex 26 can have a substantially uniform thickness, such that any light passing through the lens 20 in a forward direction is able to pass through the apex 26 without being undesirably refracted by the lens 20. Nevertheless, it is certainly within the scope of the invention to provide lens in which the thickness of the wall 28 and apex 26 differ such that one is thicker or thinner than the other.

The thickness of the lens 20 in the wall 28 and apex 26 regions is preferably in a range of about 0.1 mm to about 2 mm, more preferably in a range of about 0.2 mm to about 1 mm, and most preferably in a range of about 0.25 mm to about 0.5 mm. For example, in one embodiment of a lens 20 according to the invention, the thickness of the lens 20 in the wall 28 and apex 26 regions is 0.015" (or 0.381 mm).

The base 24 of the lens 20 is preferably configured to engage and connect with a portion of a light-curing device 40. In the present embodiment, the base 24 of the lens 20 is configured to detachably connect to a light-curing device 40 with a snap-fit connection, although other types of connections may also be used. For instance, in other embodiments, the lens 20 may be configured to engage the light-curing device 40 with a friction fit, a threaded coupling, a bayonet coupling, or any other type of coupling. The lens 20 may also be configured to fixedly engage the light-curing device 40 with an adhesive or with a mechanical bond formed during a welding procedure.

One benefit of configuring the lens 20 to be detachably connectable with the light-curing device 40 is so that the lens 20 is readily disposable and interchangeable. For instance, upon completing a dental procedure in which the lens 20 is placed within a patient's mouth, it may be desirable to dispose of the lens 20. It may also be desirable to interchange the lens 20 with alternative lenses to utilize attributes exhibited by the alternative lenses. For instance, the alternate lenses may be tinted different colors, manufactured out of different materials, or manufactured with different thickness and may, therefore, have different optical properties that may be suitable for use in different circumstances.

The lenses of the invention may be color tinted to enable filtering of light emitted from the light-curing device. It may be desirable to filter different spectrums of light depending on the type of light-curable compound that is being cured, for example. The dimensions of the conical-shaped lens may also vary between different lenses to cater to different needs and preferences.

The material composition of the lenses may also vary. According to one embodiment, the lenses may be manufactured out of any transparent material, including, but not limited to acrylic, polyacrylic, polypropylene, polycarbonate, silicone, aluminum dioxide, sapphire, quartz, and glass.

The lenses of the invention may be manufactured and sold separately or as part of a kit that includes several different lenses. The kits may include lenses having the same characteristics and properties or different characteristics and properties. The lenses of the invention may also be integrally attached to a light-curable device and sold as part of the light-curable device.

The lens 20 that is illustrated in FIG. 2 is connected to a light-curing device 40 that includes two LEDs 42. It will be appreciated, however, that the lenses of the invention may be utilized with light-curing devices having any number of LEDs or other light-generating sources. Accordingly, the light-curing device 40 that is partially illustrated in FIG. 2 exemplifies only one suitable example of a light-curing device that may utilize the lenses of the invention. (The light-curing device 40 is more fully disclosed in U.S. patent application Ser. No. 10/068,397, filed Feb. 5, 2002, entitled "Curing Light with Plurality of LEDs and Corresponding Lenses Configured to Focus Light," and is incorporated herein by reference.) In other embodiments, the lenses of the invention may also be connected with optical fiber light guides and light wands that are coupled to a light-curing device.

One particular benefit provided by the lenses of the invention is that they enable light to pass through the lens 20, particularly through the front portions of the lens 20 in the apex 26 region, without being refracted, such that the light is enabled to be emitted with a desired intensity directly in front of the apex 26. It will be appreciated that this is an advantage over other prior art lenses.

Figure 3:
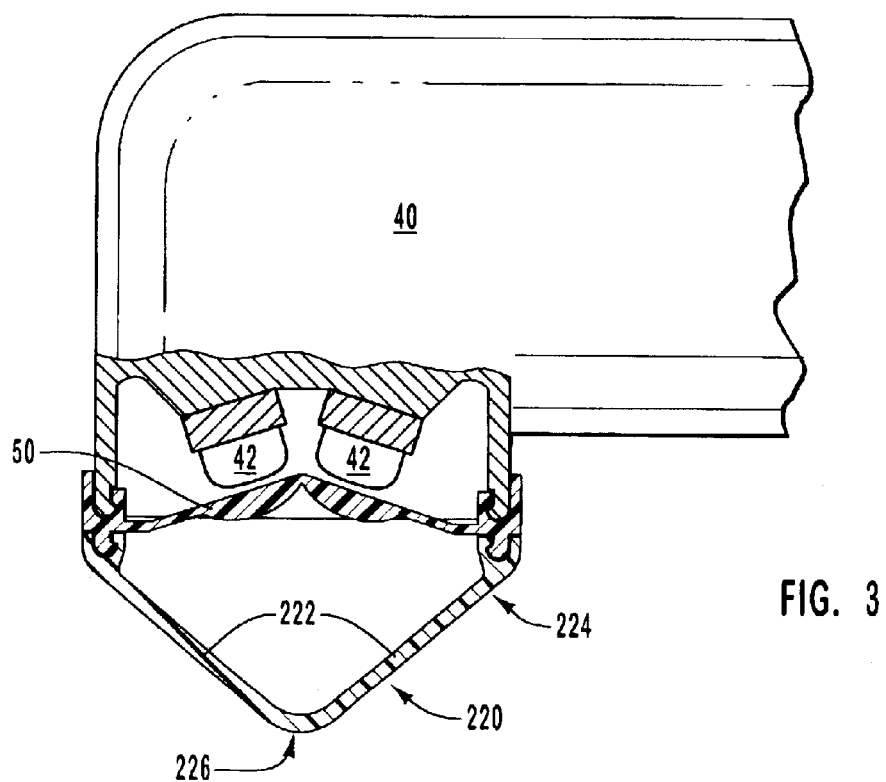
FIG. 3 illustrates one embodiment of a lens according to the invention that is configured to be connected with a light-curing device via an intermediary lens.

Although the lenses of the invention are not specifically designed to focus the light emitted from the light-curing device 40, other intermediary lenses used to focus the light may be used in combination with the lenses of the invention. One example of such an embodiment is illustrated in FIG. 3. As shown, the lens 220 in this embodiment is connected with the light-curing device 40 via an intermediary lens 50. The intermediary lens 50 is used to collimate the light that is emitted from the LEDs 42, as described in more detail in U.S. patent application Ser. No. 10/044,346, which is identified above in the Cross-Reference to Related Applications section above.

In the present embodiment, the lens 220 is configured to couple with the intermediary lens 50 with a snap-fit connection, such that the external lens 220 and the intermediary lens 50 may be detachably connected. It will be appreciated, however, that in other embodiments, the lens 220 and the intermediary lens 50 may be integrally connected. The intermediary lens 50, the light curing device 40 and any portion thereof, (e.g., the LED assembly) may also be integrally connected. As shown, the intermediary lens 50 is configured to couple with the light-curing device 40 with a snap fit type connection, although other means of connecting the intermediary lens 50 to the light-curing device 40 may also be utilized.

It will be appreciated that the light that is collimated by the intermediary lens 50 is able to pass through the external lens 220 of the invention without being undesirably refracted. This is particularly useful when treating deep dental preparations, such as Class II dental preparations.

Figure 4:
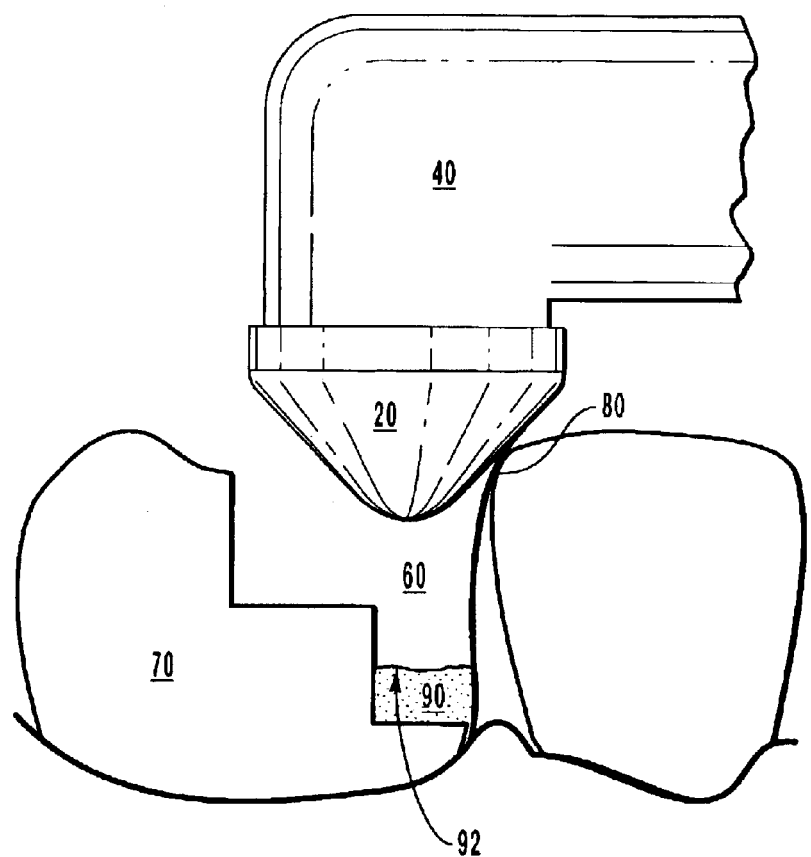
FIG. 4 illustrates one embodiment in which a lens according to the invention is inserted within a dental preparation and disposed against a matrix band.

FIG. 4 illustrates one embodiment in which a lens 20 of the invention is positioned into a deep dental preparation 60 of a tooth 70. The dental preparation 60 may represent a Class II dental preparation or any other deep dental preparation. As shown, the lens 20 is configured with a cone-shaped body that enables the lens 20 to be inserted at least partially within the dental preparation 60. Inserting the lens 20 within the dental preparation is useful for preventing the emitted light from being dispersed to other areas within the patient's mouth. The conical shape of the lens 20 can further be used to press against and manipulate uncured filling material 90 (e.g., a composite resin).

As shown, the lens 20 is also disposed against a matrix band 80 that may be used for providing form when filling the dental preparation 60. Matrix bands are well known to those of skill in the art. During the dental filling procedure, a dental filling material 90 is placed within the dental preparation 60 and cured with a suitable light-curing device. If the dental preparation 60 is very deep, the filling procedure may occur in stages, so that initially deposited dental filling material 90 can be sufficiently cured before adding new material.

For instance, in the present embodiment, the dental filling material 90 may be cured with light emitted from the light-curing device 40 before additional dental filling material is added to the dental preparation 60.

Figure 1:
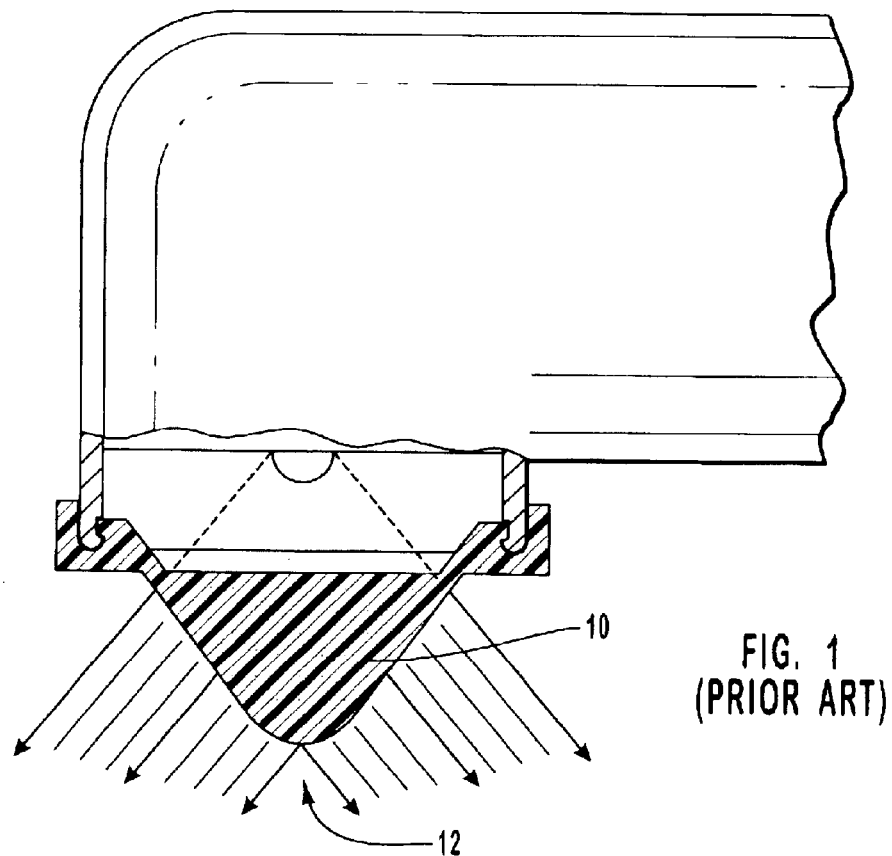
FIG. 1 illustrates a prior art lens that includes a solid conical body and that is configured for use with a light-curing device.

It will be appreciated that during certain dental filling procedures, it is necessary for the light-curing device to emit light directly in front of the apex of the lens 20 so that the dental filling material 90 can be sufficiently cured. For instance, in the present embodiment, the dental filling material 90 is disposed at location 92 that may not be radiated sufficiently unless the light-curing device is able to emit light directly in front of the lens 20. It will also be appreciated that lenses of the prior art can prevent light from being emitted directly in front of the lenses, as described above in reference to the void 12 illustrated in FIG. 1. Accordingly, the lenses of the present invention are useful and provide an advantage over the prior art lenses for at least enabling light to be emitted directly in front of the lenses.

The lenses of the invention may also be used to manipulate the light-curable compound within the dental preparation 60. For instance, once the dental preparation 60 is sufficiently filled with the dental filling material 90, the lens 20 may be used as a compression tool to work and compress the dental filling material 90 to ensure that the dental filling material 90 is properly distributed within the dental preparation 60. To facilitate this functionality, the lens 20 may be configured with a blunt and rounded apex, as shown.

In summary, the lenses of the invention are configured with a conical body having thin walls that enable light to pass therethrough without causing the light to be refracted in an undesired manner. In particular, the light is able to pass through the apex of the lenses in a forward direction and with sufficient intensity to enable the light to desirably cure the light-curable compounds disposed directly in front of the lens, and from within the dental preparation. It should be appreciated that this is an improvement over the existing lenses in the art.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A lens for use with a light-curing device and that is sized and configured to be inserted at least partially within a dental preparation, the lens comprising:
   a hollow body that has a tapered profile and that includes a hollow interior region therewithin, the hollow body comprising:
   a base circumferentially extending around the body that is configured to be connected with the light-curing device in such a manner that light emitted from the light-curing device passes through the lens when in use; and
   a wall extending outwardly from the base and converging at an apex,
   the wall and apex bounding the hollow interior region,
   the wall and apex being configured such that, when the lens is coupled to a light curing device, light emitted by the light curing device passes through the hollow interior region before reaching the apex in order for the lens to transmit an increased quantity of light emitted by the light curing device through the apex in a forward direction when in use compared to a tapered lens that does not include a hollow interior region.

2. A lens as recited in claim 1, the hollow body having a substantially conical profile in which the wall and apex define a substantially conical void as the hollow interior region.

3. A lens as recited in claim 1, wherein light emitted from the light-curing device in a forward direction passes through the lens to an area directly in front of the apex when in use.

4. A lens as recited in claim 1, wherein the hollow body comprises at least one of plastic, aluminum dioxide, sapphire, quart, or glass.

5. A lens as recited in claim 1, wherein the hollow body is comprises at least one of acrylic, polyacrylic, polypropylene, polycarbonate, or silicone.

6. A lens as recited in claim 1, wherein the hollow body is color tinted to filter selected wavelengths of light.

7. A lens as recited in claim 1, wherein the Lens is configured such that the apex can be inserted at least partially within a Class II dental preparation.

8. A lens as recited in claim 1, wherein the lens is configured to engage a light-curing device with a snap-fit connection.

9. A lens as recited in claim 1, wherein the base is configured to fixedly engage an intermediary lens that is mounted on a light-curing device.

10. A lens as recited in claim 9, wherein the lens is configured to engage the intermediary lens with a snap-fit connection.

11. A lens as recited in claim 1, wherein the wall and apex have a substantially uniform thickness such that the thickness of the wall and apex are substantially similar.

12. A lens as recited in claim 1, wherein the wall and apex have varying thicknesses.

13. A lens as recited in claim 1, wherein the wall has a thickness within a range of about 0.1 mm to about 2 mm.

14. A lens as recited in claim 1, wherein the wall has a thickness within a range of about 0.2 mm to about 1 mm.

15. A lens as recited in claim 1, wherein the wall has a thickness within a range of about 0.25 mm to about 0.5 mm.

16. A cone-shaped lens in combination with a light-curing device, the cone-shaped lens being sized and configured so as to be inserted at least partially within a dental preparation, the cone-shaped lens comprising:
   a hollow body having a substantially conical profile and defining a substantially conical void within the hollow body, the hollow body comprising:
      a base circumferentially extending around the body that is connected with the light-curing device and in such a manner that light emitted from the light-curing device passes through the lens; and
      a wall extending outwardly from the base and converging at an apex,
      the wall and apex being configured and positioned such that light emitted by the light-curing device passes through the substantially conical void before reaching the apex in order for the lens to transmit an increased quantity of light emitted by the light-curing device through the apex in a forward direction when in use compared to a tapered lens that does not include a hollow interior region.

17. A cone-shaped lens as recited in claim 16, wherein the lens is detachably connected to the light-curing device by at least one of a snap-fit, a friction fit, a threaded coupling, or a bayonet coupling.

18. A cone-shaped lens as recited in claim 16, wherein the lens is detachably connected to the light-curing device by an intermediary lens disposed between the light-curing device and the lens and wherein the lens is detachably connected to the intermediary lens.

19. A cone-shaped lens as recited in claim 16, wherein the lens is detachably connected to the light-curing device by an intermediary lens disposed between the light-curing device and the lens and wherein the lens is integrally connected to the intermediary lens.

20. A cone-shaped lens as recited in claim 16, wherein the lens is comprises at least one of acrylic, polyacrylic, polypropylene, polycarbonate, silicone, aluminum dioxide, sapphire, quartz, or glass.

21. A cone-shaped lens as recited in claim 16, wherein at least a portion of the lens is color tinted.

22. A cone-shaped lens as recited in claim 16, wherein the wall and apex have a substantially uniform thickness such that the thickness of the wall and apex are substantially similar.

23. A cone-shaped lens as recited in claim 16, wherein the wall and apex have varying thicknesses.

24. A kit for interchangeable tapered lenses for use with a light-curing device, each tapered lens being sized and configured to be inserted at least partially within a dental preparation, each tapered lens comprising:
   a hollow body that has a tapered profile and that includes a hollow interior region therewithin, the hollow body comprising:
      a base circumferentially extended around the body that is configured to be connected with the light curing device in such a manner that light emitted from the light curing device is enabled to pass through the lens; and a wall extending outwardly from the base and converging at an apex,
   the wall and apex being configured such that, when coupled to a light-curing device, the lens is able to transmit an increased quantity of light emitted by the light-curing device through the apex in a forward direction when in used compared to a tapered lens that doe not include a hollow interior region,
   the wall and apex bounding the hollow interior region, the wall and apex being configured such that, when the lens is coupled to light-curing device, light emitted by the light curing device passes through the hollow interior region before reaching the apex in order for the lens to transmit an increased quantity of light emitted by the light-curing device through the apex in a forward direction when in use compared to a tapered lens that does not include a hollow interior region.

25. A kit as recited in claim 24, wherein each tapered lens is detachably connectable with the light-curing device by at least one of a snap-fit, a friction fit, a threaded coupling, or a bayonet coupling.

26. A kit as recited in claim 24, wherein at least one of the lenses in the kit comprises at least one material selected from the group comprising acrylic, polyacrylic, polypropylene, polycarbonate, silicone, aluminum dioxide, sapphire, quartz, and glass.

27. A kit as recited in claim 24, wherein at least one of the lenses in the kit is color tinted.

28. A kit as recited in claim 24, wherein at least one of the lenses in the kit has a substantially conical profile.

* * * * *